(12) United States Patent
Furtak

(10) Patent No.: US 6,384,916 B1
(45) Date of Patent: May 7, 2002

(54) PARALLEL DETECTING, SPECTROSCOPIC ELLIPSOMETERS/POLARIMETERS

(76) Inventor: Thomas E. Furtak, 15927 W. Ellsworth, Golden, CO (US) 80401

(*) Notice: Subject to any disclaimer, the term of this patent is extended or adjusted under 35 U.S.C. 154(b) by 0 days.

(21) Appl. No.: 09/715,921

(22) Filed: Nov. 17, 2000

Related U.S. Application Data (63) Continuation of application No. PCT/US00/20417, filed on Jul. 27, 2000.
(60) Provisional application No. 60/146,044, filed on Jul. 27, 1999.

(51) Int. Cl.$^7$ ................................................ G01J 4/04
(52) U.S. Cl. ........................................................ 356/369
(58) Field of Search ................................ 356/369, 364, 356/365, 366, 367, 368; 250/225

(56) References Cited

U.S. PATENT DOCUMENTS

| | | | |
|---|---|---|---|
| 4,681,450 A | | 7/1987 | Azzam |
| 4,850,711 A | | 7/1989 | Sano et al. |
| 5,081,348 A | | 1/1992 | Siddiqui |
| 5,102,222 A | | 4/1992 | Berger et al. |
| 5,198,875 A | | 3/1993 | Bazin et al. |
| 5,311,285 A | | 5/1994 | Oshige et al. |
| 5,335,066 A | | 8/1994 | Yamada et al. |
| 5,337,146 A | | 8/1994 | Azzam |
| 5,596,411 A | * | 1/1997 | Fanton et al. ................ 356/369 |
| 5,610,392 A | * | 3/1997 | Nagayama et al. ......... 356/381 |
| 5,793,480 A | | 8/1998 | Lacey et al. |
| 5,910,841 A | | 6/1999 | Masao |

OTHER PUBLICATIONS

Hunderi, On the Problems of Multiple Overlayers . . . , Surface Science 61 (1976), pp 515–520.

Aspens et al., Investigation of Effective–Medium Models., 1979 Physical Review B, pp. 3292–3302.

Azzam, Division of Amplitude Photopolarimeter . . . , Optica Acta, 1982, vol. 29, #5 pp. 685–689.

Azzam et. al., Construction, Calibration . . . , Sep. 28, 1987, Rev.Sci.Instrum, vol. 59, #1, Jan. 1988, pp. 84–88.

Jellison, Four–Channel Polarimeter for Time . . . , 1987 Optics Letters/vol. 12, #Oct. 10, 1987, pp. 766–768.

Azzam et. al., Accurate Calibration of the Four . . . vol. 6, #Oct. 10, 1989 J.Opt.Soc.Am.A, pp. 1513–1521.

Todorov et. al., Spectrophotopolarimeter: Fast . . . Optics Letters/vol. 17, #5;/Mar. 1, 1992, pp. 358–359.

Azzam et. al., Construction, Calibration, and . . . Rev. Sci. Instrum., vol. 59, #1, 1/88, pp. 84–88.

Collins, et. al., Real Time Spectroscopic Elliosometry . . . Thin Solid Films, 233 (1993), pp. 244–252.

\* cited by examiner

*Primary Examiner*—Hoa Q. Pham
(74) *Attorney, Agent, or Firm*—Donald W. Margolis (57) ABSTRACT

The parallel detecting spectroscopic ellipsometer/polarimeter sensor has no moving parts and operates in real-time for in-situ monitoring of the thin film surface properties of a sample within a processing chamber. It includes a multi-spectral source of radiation for producing a collimated beam of radiation directed towards the surface of the sample through a polarizer. The thus polarized collimated beam of radiation impacts and is reflected from the surface of the sample, thereby changing its polarization state due to the intrinsic material properties of the sample. The light reflected from the sample is separated into four separate polarized filtered beams, each having individual spectral intensities. Data about said four individual spectral intensities is collected within the processing chamber, and is transmitted into one or more spectrometers. The data of all four individual spectral intensities is then analyzed using transformation algorithms, in real-time.

14 Claims, 7 Drawing Sheets

PARALLEL DETECTING, SPECTROSCOPIC ELLIPSOMETERS/POLARIMETERS

This application is a continuation of PCT/US00/20417, filed Jul. 27, 2000, which claims benefit of Ser. No. 60/146,044, filed Jul. 27, 1999.

GOVERNMENT LICENSE RIGHTS

This invention was made with Government support under contract number DAAH01-96-C-R302 awarded by the U.S. Army, under Agreement No. MDA 972-95-3-0036 awarded by DARPA, and under subcontract number ZAX-8-17647-11 under prime contracts DE-AC36-83 CH10093 and DE-AC36-98GO10337 awarded by the Department of Energy. The Government has certain rights in this invention.

BACKGROUND OF THE INVENTION a). Technical Field

This invention relates generally to parallel detecting spectroscopic ellipsometer/polarimeter instruments that are capable of determining the polarization state of light over a wide range of wavelengths, in particular, after the light has interacted with a sample. The parallel detecting spectroscopic ellipsometer/polarimeter provides spectroscopic polarization information by simultaneously measuring four specific polarization states of the light with an optical configuration that requires no moving parts. The spectroscopic polarization information, which is so collected, can be used to provide real-time information about the sample through the use of advanced interpretive algorithms.

b). Background Art

The polarization effects of light reflected from surfaces has been studied since the early $19^{th}$ century. In general, the term ellipsometry usually applies to analysis of light reflected from a surface, where the reflected light must be in a well defined pure state of elliptical polarization. More specifically, the term "ellipsometer," is based on the phenomenon that the electric field vector of light reflected from a sample surface forms an ellipse in a time resolved wave due to the polarized light components parallel and perpendicular to the sample surface interacting in different ways and usually applies to analysis of reflected light where the light must be in a well defined pure state of elliptical polarization,. The term "polarimeter" is less well defined, but is usually applied to analysis of transmitted or scattered light. In general polarimetry determines the complete polarization state of light, including the capability to detect non-polarized components. The change in the polarization state of light measured by an ellipsometer after interacting with a material, is extremely sensitive to the properties of the material, including the thickness of a film, its electronic energy states, its surface roughness and morphology, its composition, and defect densities.

In a typical ellipsometer installation, light in a collimated beam passes through a linear polarizer that is oriented so that the optical electric field has components parallel and perpendicular to the plane of incidence of the material sample with which it will interact. After the interaction of the light with the sample, the relative amplitudes and phases of the components parallel and perpendicular to the plane of incidence of the material sample are changed. An ellipsometer measures changes in the relative amplitudes and phases between the parallel "p" and perpendicular "s" electric field components of a light beam, and more specifically of a polarized light wave, as it reflects from a sample surface. These parameters are traditionally expressed as $\psi$ and $\Delta$, which are related to the ratio ($\rho$) of the reflectance coefficients for the p and s optical electric fields, ie. $\rho = \tan(\psi) e^{i\Delta} = r_p/r_s$. Unlike a reflectance/transmittance measurement, which only provides the ratio of reflected/transmitted to incidence irradiances, an ellipsometer can extract both real and imaginary parts of the dielectric function of the sample, ($\epsilon_1, \epsilon_2$), as a function of photon energy, hv, from the $\psi$ and $\Delta$. However, due to the huge computational demands and the extremely tedious measurements, polarimetry and ellipsometry did not find a large number of applications until the second half of the $20^{th}$ century, when automation and computers become readily available. A good history of ellipsometry in presented by R. M. A. Azzam, "Selected Papers on Ellipsometry," SPIE Milestone Series, Vol. MS 27, SPIE, Bellingham, Wash. (1991).

Since the 1960's, literally thousands of ellipsometry/polarimetry papers and patents have been written discussing hundreds of applications and instrument designs. The advent of spectroscopic ellipsometry (D. E. Aspnes, J. B. Theeten, F. Hottier, "Investigation of the effective-medium models of microscopic surface roughness by spectroscopic ellipsometry," Phys. Rev. B, 1979) and variable incident angle measurements (O. Hunderi, "On the problems of multiple overlayers in ellipsometry and a new look at multiple angle of incidence ellipsometry," Surface Science 1976) has greatly added to the large interest as well. From an instrumentation standpoint, three basic approaches have been followed to measure the polarization state of light, "null", "rotating analyzer" and "polarization filter" ellipsometers. The first instruments that measured polarization used true nulling methods that required a phase shifter as well as a polarizer to determine the light's polarization state. Modern day equivalent instruments determine the complex reflectance change, $\rho$, by sampling the intensity of the reflected light after it passes through a second polarizer, called the "analyzer", whose orientation changes in a continuous fashion. The detected signal is a sinusoid as a function of the orientation angle (R. W. Collins, I. An, H. V. Nguyen, and Y. Lu, "Real-time spectroscopic ellipsometry for characterization of nucleation, growth, and optical functions of thin films", Thin Solid Films, V. 233, (1993), p. 244). Although phase and amplitude of that sinusoid can be analyzed to extract $\psi$ and $\Delta$, the data needs to be acquired as a function of time, with each analyzer orientation taking a finite time interval to acquire. Even with a continuously rotating analyzer and triggered detection system, data are acquired serially or sequentially as a function of the phase angle of the analyzer. This type of system can acquire spectroscopic data, primarily by passing incident white light through a monochrometer that provides a single wavelength of light. This single wavelength of incident light directed through a polarizer is reflected off of the sample, then through an analyzer and is detected with a photodetector. Additional wavelengths are selected with a monochrometer, and the ellipsometry data is serially acquired as a function of those wavelengths. For either single wavelength or multiple wavelength (spectroscopic) cases, the main problem with the use of such "rotating analyzer" instrinents is that the data is acquired serially, and typically takes several seconds to measure a data point at a single wavelength.

Polarization filter instruments primarily related to polarimetry, divide the light into multiple components to enable a complete or partial determination of the polarization state. In the 1970's photopolarimeters were designed for astronomy applications in which modulation of polarizing optics were used to determine polarization states of the light. Several photopolarimeter instruments based on simultaneous measurement of different polarizations of the light have been designed since then, including R. M. A. Azzam. "Division of amplitude photopolarimeter for the simultaneous including R. M. A. Azzam, "Division of amplitude photopolarimeter for the simultaneous measurement of all four Stokes parameters of light," Optica Acta Vol. 29, pg. 685 (1982), G. E. Jellison, "Four channel polarimeter for time resolved ellipsometry, Opt. Lett., Vol. 12, Pg. 766 (1985), Azzam U.S. Pat. No. 4,681,450; Siddiqui U.S. Pat. No. 5,081,348; Berger et al. U.S. Pat. No. 5,102,222; Yamada et al. U.S. Pat. No. 5,335,066, and Lacey et al. U.S. Pat. No. 5,793,480. The basic polarization filter designs involve polarization dependent splitting of the light into several components that are measured simultaneously with multiple detectors. The collected intensities are then analyzed to determine the polarization state of the incoming light.

Azzamn and Jellison, supra, have developed photopolarimeters that split the light to be analyzed into different beams using appropriately coated optics. The output signals are collected with detectors, primarily photodetectors that do not discriminate frequency, and some or all of the parameters that characterize the polarization state of the monochromatic light is calculated using the measured intensities and an instrument matrix. Typically, the detected polarization intensities are linearly related to the four "Stokes" parameters that more traditionally characterize the polarization state of the light. Through a calibration operation the 16 coefficients of this linear relationship can be determined. The coefficients can be represented by a 4×4 matrix, referred to as the "instrument matrix" that compactly expresses the transformation of the detected intensities into the four Stokes parameters.

Azzam U.S. Pat. No. 4,681,450 discloses an optical polarimeter that uses the reflection off three different photodetectors to change the polarization state of the single wavelength light for the next photodetector. Siddiqui U.S. Pat. No. 5,081,348 discloses an optical polarimeter having four channels which provides a method and apparatus for rapidly determining the polarization state of an incoming beam of single wavelength light, primarily from an optical fiber; in which four separate portions of the beam are passed simultaneously through four Stokes filters. Berger et al. U.S. Pat. No. 5,102,222 discloses a system for single wavelength light wave polarization determination using a hybrid system for determining polarization vector components (Stokes parameters) that includes beam splitters. The use of two splitters and four detectors allows reconstruction of the polarization state.

Of greatest interest is Yamada et al. U.S. Pat. No. 5,335,066, which discloses an ellipsometric system and method. In the claimed invention, the light source is taught to be a single wavelength linearly polarized laser beam, that is reflected from a sample as a beam which is passed through splitters and polarizers so as to detect the polarization state of the light by means of four intensities. These intensities are converted by the associated software into $\psi$ and $\Delta$ at the single wavelength of the laser. In use, the smallest detected intensity is discarded when determining ellipsometric parameters, e.g. surface conditions. However this limits the amount of information obtained since the complete polarization state of the light is not determined.

Lacey et al. U.S. Pat. No. 5,793,480 discloses a combined interferometer/ellipsometer for determining the space between a transparent member, such as a glass disc, and a reflective surface, and for determining the real and imaginary parts, n and k, of the index of refraction. The single wavelength reflected light is divided into separate beams; two beams are used for interferometry measurements to determine the air gap, while a third is used in conjunction with the other two to determine n and k.

While all of the division of amplitude systems in the prior art discussed to this point can collect data over a range of wavelengths, they can only collect one wavelength at a time and require separate calibration at each wavelength. Only two of the references teach about collecting multiple wavelengths simultaneously with division of amplitude instruments. These are Azzam U.S. Pat. No. 5,337,146 and T. Todorov and L. Nikolova, "Spectrophotopolarimeter: fast simultaneous real-time measurement of light parameters," Optics Lett., Vol. 17, pg. 358 (1992), which teaches how a grating can be used in conjunction with other polarizing optics to determine the polarization state of light by using a technique that involves measuring multiple order diffraction reflections with four or more detectors. The diffraction grating separates the light into individual frequency components, so that if additional photodetectors or photo-detecting arrays are used, then multiple wavelength data may be obtained. The main problem with using these systems in their preferred embodiment is that they have substantial position and alignment sensitivity that will be associated with the spatially resolved light after it is reflected from the diffraction grating. While this problem may be overcome at a single wavelength, it is virtually impossible to solve for simultaneous detection of multiple wavelengths.

Several parameters, such as the polarizer azimuth and the angle of incidence, have to be determined with a calibration procedure before the ellipsometer can be used effectively. Several calibration methods, e.g. Tompkins, Harland and McGahan, William, Spectroscopic Ellipsometry and Reflectometry, John Wiley & Sons, Inc., 1999, have been used in the past for different ellipsometers, but the different optical components used for each type requires an unique calibration procedure. Typically, calibration procedures for polarimeters and spectroscopic ellipsometers are tedious and time consuming. For example, the calibration methods discussed by Azzam, R. M. A and Masetti, E. and Elminyawi, I. M. and EI-Saba, A. M., "Construction, calibration, and testing for a four-detector photopolarimeter", Rev. Sci. Insrun., Vol. 59, 1988, pp. 84–88 and Azzam, R. M. A. and Lopez, A. G., "Accurate calibration of the four-detector photopolarimeter with imperfect polarizing elements", J. Opt. Soc. Am., Vol. A 6, 1989, pp 1513–1521, namely the "four-point calibration method" and the "equator-poles calibration methods", are time consuming since they are only appropriate for calibrating a single wavelength at a time. In the four-point calibration method four linearly independent input states are used for calibration at a given wavelength. Thus the procedure has to be repeated for each of the wavelengths under consideration. In the equator-poles method the output intensities are recorded as a function of linearly polarized light azimuth over one period for a given wavelength and fitted to a 3-term Fourier series. Again, this procedure has to be repeated for all the wavelengths of interest and cannot be used for broad wavelength applications.

It is thus seen that the calibration procedures of the ellipsometers of the prior art are complex and inefficient, and that they are incapable of simultaneously determining the calibration parameters for the entire spectral range of the instrument, and they require a substantial amount of time for each calibration. More specifically, none of these prior art references teaches or suggests a combined parallel detecting, spectroscopic ellipsometer/polarimeter sensor system using four state polarization filtering in a manner which substantially decreases spectroscopic polarization data collection time, which also provides true multispectral analysis of polarization data, in real-time, using advanced transformation algorithms for thousands of wavelengths simultaneously, nor are of a design which allows them to be integrated within a processing chamber. In addition, none of the state-of-the-art spectroscopic ellipsometers are capable of polarimetry or simultaneous collection of polarization state information. Accordingly, there exists a need for a spectroscopic ellipsometer/polarimeter system that provides these capabilities.

DISCLOSURE OF THE INVENTION

It is thus an object of the present invention to provide a system and calibration procedure for a parallel detecting spectroscopic ellipsometer/polarimeter which is simple and efficient, and capable of simultaneously determining the calibration parameters over a wide spectral range.

It is a further object of the present invention to provide such a system and calibration procedure for a parallel detecting spectroscopic ellipsometer/polarimeter that requires a fraction of the time compared to the calibration of other polarimeters and spectroscopic ellipsometers.

It is yet a further object of the present invention to provide such a system and calibration procedure for a parallel detecting spectroscopic ellipsometer/polarimeter that is performed in three steps, as detailed below, and which minimize the need for recalibration.

The present invention consists of a parallel detecting spectroscopic ellipsometer/polarimeter instrument that completely determines the polarization state of light. In preferred embodiments the light that is analyzed has a wavelengths from about 200 nm to about 5000 nm after the light has interacted with a sample, although light of other wavelengths can be analyzed. The ultimate spectral range is dependent upon available and future spectrometers and spectroscopic measuring techniques. Thus the spectral range is limited only by available detectors and is not intrinsically limited by the instrument itself. Thus, one could apply the same parallel and spectroscopic detection system for higher and lower light energies, including ultraviolet, x-rays, synchrotron radiation, far IR and even longer wavelength applications.

The parallel detecting spectroscopic ellipsometer/polarimeter system of the present invention provides spectroscopic polarization information by simultaneously measuring four specific polarization states of the light with an optical configuration that has no moving parts. The spectroscopic polarization information is collected in as little as 5 ms (limited only by detector technology, not the design of the instrument) and provides real-time information about the sample through the use of advanced interpretive algorithms in less than 20 ms. The parallel detecting, spectroscopic ellipsometer/polarimeter system of the present invention includes, generally, an electromagnetic radiation beam, including a wide spectrum of wavelengths from a single collimated source, the light beam. The light beam from the single collimated light source is directed through polarizing optics and thence impinges upon a surface that is being studied or monitored, typically a thin-film on a substrate support. The light beam that is reflected from the surface is then split into two beams by a first beam splitter. Then, a second and third splitter further splits each of those two beams into a total of four beams. The four resulting beams are then directed to pass through different polarization filters, and/or quarter wave plates to provide data for monitoring the condition of the surface of the sample from which they were reflected, all in real time.

As set forth in greater detail below, the system and its components are designed and sized to fit within a thin film processing chamber, such as a vacuum deposition chamber. It could be made even smaller, for example using integrated optics. The system is capable of supplying, in real time, any of the various valuable units of information that can be extracted through the technique of spectroscopic ellipsometry, such as monitoring the rate of growth, and/or the thickness, the microstructure, the surface morphology, the presence of voids, the existence of fractures, the composition of the sample, combinations of the foregoing, and so on, of the sample, for example during its formation by any film formation process. Ancillary to the process, human or software monitoring of thin-film growth, and termination of the thin film formation process may be practiced when the desired film properties or thickness are detected.

The parallel detecting spectroscopic ellipsometer/polarimeter of the present invention provides four combined features into a single system. These include the analysis of four channel polarization data using different polarization filters, and/or quarter wave plates, and of a system for multispectral processing of the four channels. Then, advanced transformation algorithms are used to subject the raw spectral data to provide specific and detailed analysis, in real-time. In the practice of the present invention, all of these components are assembled into a compact unit that is designed to allow it to be mounted inside of, for example, a thin film processing chamber. By combining all four of these features into a single compact package, the parallel detecting spectroscopic ellipsometer/polarimeter of the present invention provides advanced and unique capabilities that no currently known instrument is capable of performing. These capabilities include better than an order of magnitude decrease in spectroscopic polarization data collection times, as compared to state-of-the-art spectroscopic ellipsometers and true spectroscopic analysis of polarization data at thousands of wavelengths simultaneously, as compared to single wavelength division of amplitude polarimeters. The parallel detecting spectroscopic ellipsometer/polarimeter of the present invention is also of such a design and size that it is capable of being integrated within a standard size thin film processing chamber. This enables it to be inexpensively adapted for a variety of materials applications, even if the processing chamber in which it is placed had been originally designed without external optical access to the sample. The sensor system of the present invention is referred to as a parallel detecting, spectroscopic ellipsometer/polarimeter, because it measures the full Stokes vector, that is all four Stokes parameters, that can be translated into $\psi$, $\Delta$, intensity, and depolarization information for thousands of wavelengths. Thus, the instrument is also capable of polarimetry, of which ellipsometry is a subset or species.

The parallel detecting spectroscopic ellipsometer/polarimeter of the present invention detects four polarization states that can be expressed in terms of the four Stokes parameters:

$$S_0 = a_s^2 + a_p^2,\ S_1 = a_s^2 - a_p^2,\ S_2 = a_s a_p \cos(\phi_p - \phi_s),\ S_3 = a_s a_p \sin(\phi_p - \phi_s)$$

where, a and $\phi$ are the amplitude and phase, and s and p denote optical field orientation in the planes parallel and perpendicular to the plane of incidence, respectively. To determine the four Stokes parameters, intensities from the four spectrometers are linearly transformed using a pre-calibrated, 4×4, "instrument" transfer matrix ($\vec{I}=A\vec{S}$). A data set, consisting of the four Stokes parameters as a function of wavelength, can then be used to determine complex reflectance and/or $\psi$ and $\Delta$, and also provides information about the depolarization of the light, a capability no other rotating polarizer based spectroscopic ellipsometer possesses. Depolarization information can be used to more easily and directly measure surface roughness, interfacial mixing, and other features that cause the light to become unpolarized. This choice of polarization state measurements is significantly different from present state-of-the-art spectroscopic ellipsometers that measure only polarized light in a serial fashion and cannot measure depolarization directly. Thus, the present invention is the first known instrument to measure the complete polarization state of the light, including depolarization, spectroscopically. The parallel detecting of the polarization states significantly decreases the time required to make a measurement and eliminates the random and systematic errors associated with signal drift or interference that occur with conventional ellipsometry measurements taken over a period of time. Therefore, the simultaneous detection of the present invention significantly enhances the intrinsic precision of spectroscopic ellipsometry. Furthermore, by simply modulating the incident polarization state, the system of the present invention is capable of measuring the entire Mueller matrix of the sample at each wavelength, rather than only measuring the Stokes vector of polarized light reflected from a sample. This is of substantial value as the Mueller matrix provides additional data that enables the determination of the polarization modification characteristics of the sample, and this data can then be translated into valuable information for materials engineers. In addition, the system of the present invention also measures the intensity of the light after it interacts with the sample. Therefore, by simply measuring the incident intensity of the reflected light, the sensor system of the present invention also provides spectroscopic reflectometry measurements.

As noted above, the sensor system of the present invention provides multispectal wavelength analysis of four channel polarization data, as compared to existing polarimeters that only measure polarization of a single wavelength at a time, defined, for example by a filter at the light source or by a laser source. The multispectral wavelength nature of the parallel detecting spectroscopic ellipsometer/polarimeter sensor system of the present invention required unique design innovations. These include accurate alignment of collected light into four polarization-state channels that deliver the multi-wavelength light into spectrometers, the removal of wavelength dependence of the optical components from the measurement, and the removal of, or the need to calibrate, polarization changes as a function of wavelength from optical components and geometries when making the measurement. This is accomplished in preferred embodiments of the parallel detecting spectroscopic ellipsometer/polarimeter of the present invention in two ways. First, a calibration scheme is provided that removes the polarization and wavelength dependence of the optical components and provides an intensity independent normalization that does not require prior knowledge of the angle of incidence. Then, a mechanism, such as fiber optic cables coupled through position desensitizing optics, is used to collect the individually polarized multi-wavelength intensities and deliver them to the spectrometers. While it is possible to place the spectrometers directly with collection optics, the use of fiber optics enables the spectrometers, that may be more sensitive to the harsh environments where the polarization measurements are taking place, to be decoupled from the parallel detecting spectroscopic ellipsometer/polarimeter detection head, and therefore removes the requirement for accurate alignment of the spectrometers to the detection optics. This means that, for the first time, polarization measurements with a parallel detecting spectroscopic ellipsometer/polarimeter can be made close to samples in harsh environments, e.g. inside a vacuum chamber which has significantly elevated temperatures, for example due to high energy deposition of materials and resulting substrate heating. No currently known polarimeter or ellipsometer provides this flexibility while also providing the complete determination of the optical properties of the sample which is undergoing analysis, as does the parallel detecting spectroscopic ellipsometer/polarimeter of the present invention. All other instruments require an accurately aligned optical window to perform measurements inside a processing chamber. This adaptability and complete characterization capability of the parallel detecting spectroscopic ellipsometer/polarimeter sensor of the present invention enable it to be used for new applications previously not allowed by existing polarimeters and ellipsometers due to their strict geometric and physical limitations. In addition, the parallel detecting spectroscopic ellipsometer/polarimeter sensor of the present invention can be installed into processing chambers that were originally not designed to accommodate optical monitoring.

In addition to providing complete measurement of optical properties in a parallel detecting spectroscopic ellipsometer/polarimeter sensor having no moving parts and in real time, the sensor of the present invention is designed to include a multitude of unique alignment concepts. These include the use of a dual laser/quadrant photodiode system that establishes a well-defined geometrical relationship between the sample and the optical heads. This ensures accurate handling of the optical beam within the head. In addition, CCD (charge couple device) cameras may be used for alignment of the actual reflected beam. Furthermore, the use of a corner cube and double reflection from the sample eliminates the need for a source head by combining both the source and detection head into a single unit. This further simplifies the optical access to the sample and makes it possible to adapt the parallel detecting spectroscopic ellipsometer/polarimeter to chambers that may preclude installation within the processing environment. Finally, the use of diffusers, defocusing, and physically larger source beams decrease alignment sensitivity while maintaining measurement precision and accuracy.

As noted above, the use of advanced transformation algorithms is also an essential component of the parallel detecting spectroscopic ellipsometer/polarimeter system of the present invention. Such advanced transformation algorithms provide real-time intelligent process control. These algorithms are based on a number of increasingly complex interpretation schemes, including models. Such exact models are developed from first principles with data reduction. An empirical model may be created from exact optical property measurements from actual materials of interest. Models may be developed from combinations of both exact and empirical models. Models may be developed using data transformation: which is based on regression algorithms, or on spectral fingerprint type analysis, or on heuristic algorithm training techniques, e.g., neural networks. The specific interpretation scheme used with the models will depend upon the specific material properties needed, and where appropriate, for intelligent process control and required on-line quality control.

Not only can standard polarimetry, ellipsometry, and reflectometry information be provided by the parallel detecting spectroscopic ellipsometer/polarimeter of the present invention at multiple incident angles, but additional configurations can be used to obtain additional information. Some of these configurations include replacing the spectral distribution with information delineated according to other characteristics. For example, reference to multiple angle collection of the outgoing light from the sample can be used to perform forward scattering analysis of the surface interaction, thereby providing valuable information about the surface topography, grain structure, and other contributions to scattering.

The system may also image an illuminated line on the sample surface onto up to four CCD cameras, thereby detecting the light through up to four polarization-filtered channels. This would yield a spectral fingerprint of the surface along the line and having spatial resolution that could approach 5 microns. By extending this idea to a general light collector, while giving up the spectral data, one could obtain a two-dimensional image of the polarization modification characteristics of the sample and therefore perform a broad range of imaging polarimetry measurements. Additional combinations of optics and optical properties integrated directly into the fiber optics could result in additional size reduction and optical path simplification.

These and other objects of the present invention will become apparent to those skilled in the art from the following detailed description, showing the contemplated novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF DRAWINGS

The accompanying drawings illustrate complete preferred embodiments of the present invention according to the best modes presently devised for the practical application of the principles thereof, and in which.

BEST MODE FOR CARRYING OUT THE INVENTION AND INDUSTRIAL APPLICABILITY

1. Optical Configuration

Figure 1:
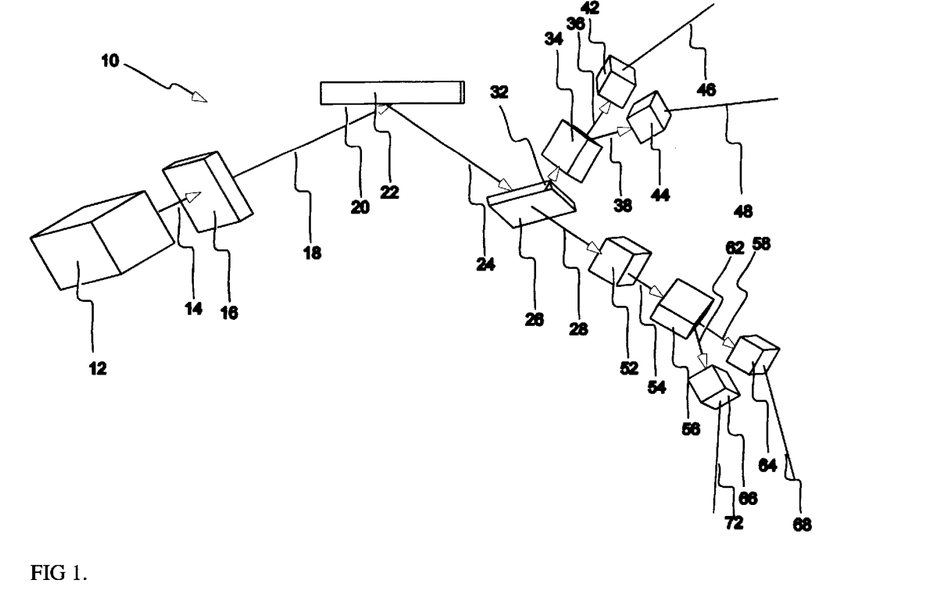
FIG. 1 is a schematic representation of one embodiment of the parallel detecting spectroscopic ellipsometer/polarimeter optical system of the present invention.

As illustrated in the embodiment of FIG. 1, the present invention is a parallel detecting spectroscopic ellipsometer/polarimeter, generally 10, for use, for example for real-time, in-line monitoring of thin film deposition in vacuum. The system includes a source 12 for a beam of radiation 14. In preferred embodiments the beam of radiation is in the form of a light beam from a single collimated light source, the light beam including a wide spectrum of wavelengths, such as white light in the range of about 200 nm to about 5000 nm. In preferred embodiments, the light source is a tungsten halogen or xenon arc lamp, although other broad wavelength sources of radiation in different ranges may be used. Beam 14 is then passed through a polarizing filter 16 to convert it to a polarized beam of light 18. The polarized beam of light 18 then contacts the surface 20 of sample 22 at an angle, and interacts with and is reflected from the sample surface 20. The polarization state of beam 18 is changed due to a number of intrinsic material properties of sample surface 20, and is reflected as modified, information carrying polarized beam 24. Information carrying polarized beam 24 is then passed through a first beam splitter 26 and divided into two beams 28 and 32. Beam 32 is in turn then passed through a polarizing beam splitter 34 to produce further polarized beams 36 and 38. Polarized beams 36 and 38 are then each received by optic fiber couplers 42 and 44, respectively, which include lens and alignment sensitivity attenuators. From there they are then fed through fiber optic cables 46 and 48, respectively, through an integrated grating-based multi-channel spectrometer or photodiode array detector, not shown.

Simultaneously, beam 28 is passed through a quarter wave plate 52 in order to undergo orthogonal rotation, to produce beam 54. Beam 54 is in turn then passed through a second polarizing beam splitter 56 to produce further rotated polarized beams 58 and 62. Polarized beams 58 and 62 then each received by optic fiber couplers 64 and 66, respectively, which also include lens and alignment sensitivity attenuators. From there they are then fed through fiber optic cables 68 and 72, respectively, through a pair of integrated grating-based multi-channel spectrometer or photodiode array detector, not shown. As with the other receivers, the position sensitive detector decodes the wavelength-dependent intensity by electronically reading the spectral signature as it is dispersed on the detector surface, and the resulting data, along with the data from the other two fiber optic cables 46 and 48 is processed with a predetermined instrument matrix and interpreted with advanced transformation algorithms.

Figure 2:
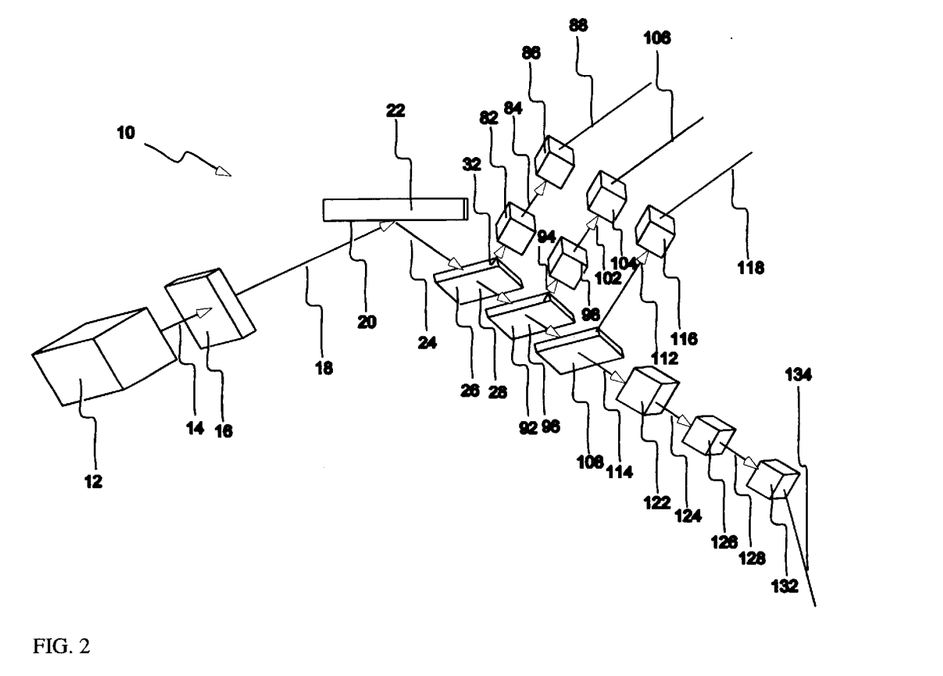
FIG. 2 is a schematic representation of another embodiment of the parallel detecting spectroscopic ellipsometer/polarimeter optical system of the present invention.

The modified system of the present invention that is illustrated in FIG. 2 also illustrates a parallel detecting spectroscopic ellipsometer/polarimeter, generally 10, in which like numbers refer to like elements, as in FIG. 1. However, in this embodiment, split polarized beam 32 passes through polarizer 82 in order to undergo orthogonal rotation, to produce beam 84. Beam 84 is in turn then received by optic fiber coupler 86, which includes lens and alignment sensitivity attenuators. From there the signal is then fed through fiber optic cable 88 through an integrated grating-based multi-channel spectrometer or photodiode array detector, not shown.

Split beam 28 is simultaneously sent through beam splitter 92 to produce equivalent beams 94 and 96. Split polarized beam 94 passes through polarizer 98 in order to undergo orthogonal rotation, to produce beam 102. Beam 102 is in turn then received by optic fiber coupler 104, which includes lens and alignment sensitivity attenuators. From there the signal is then fed through fiber optic cable 106 through a second integrated grating-based multi-channel spectrometer or photodiode array detector, not shown. Similarly, split beam 96 is simultaneously sent through beam splitter 108 to produce beams 112 and 114. Split beam 112 is in turn then received by optic fiber coupler 116, which includes lens and alignment sensitivity attenuators. From there the signal is then fed through fiber optic cable 118 through a third integrated grating-based multi-channel spectrometer or photodiode array detector, not shown.

Finally, split beam 114 is passed through a quarter wave plate 122 to undergo orthogonal rotation, to produce beam 124. Beam 124 is in turn received by polarizer 126 to produce beam 128 which is in turn received by optic fiber coupler 132 and then fed through fiber optic cable 134 through a fourth integrated grating-based multi-channel spectrometer or photodiode array detector, not shown. As with the other receivers, a position sensitive detector decodes the wavelength-dependent intensity by electronically reading the spectral signature as it is dispersed on the detector surface. The resulting data, along with the data from the other three fiber optic cables 88, 106 and 118 is processed with a predetermined instrument matrix and interpreted with advanced transformation algorithms.

2. Data Collection and Interpretation

Figure 3:
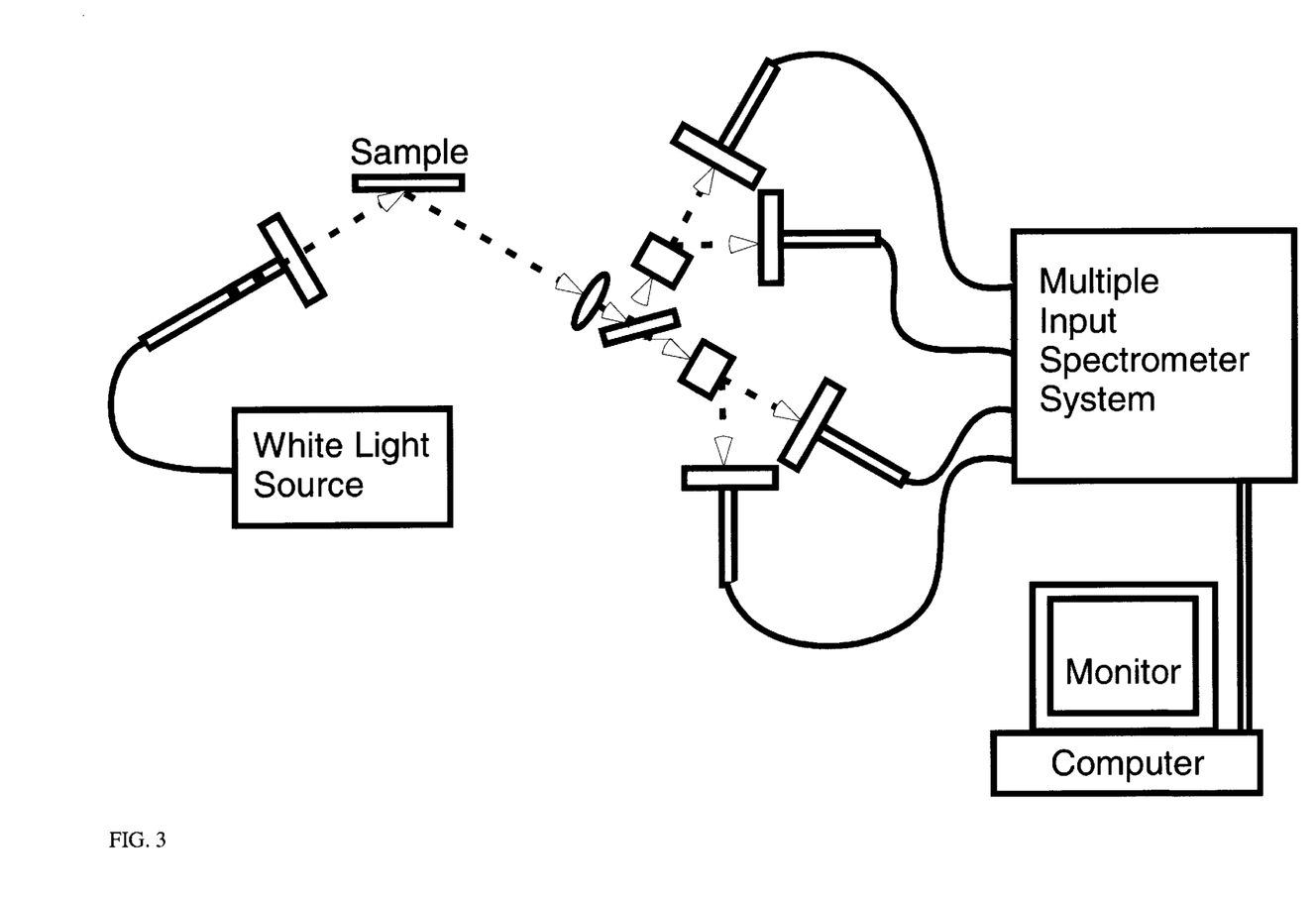
FIG. 3 is a schematic representation of the apparatus showing one embodiment of the entire parallel detecting spectroscopic ellipsometer/polarimeter system of FIG. 1 of the present invention.
Figure 4:
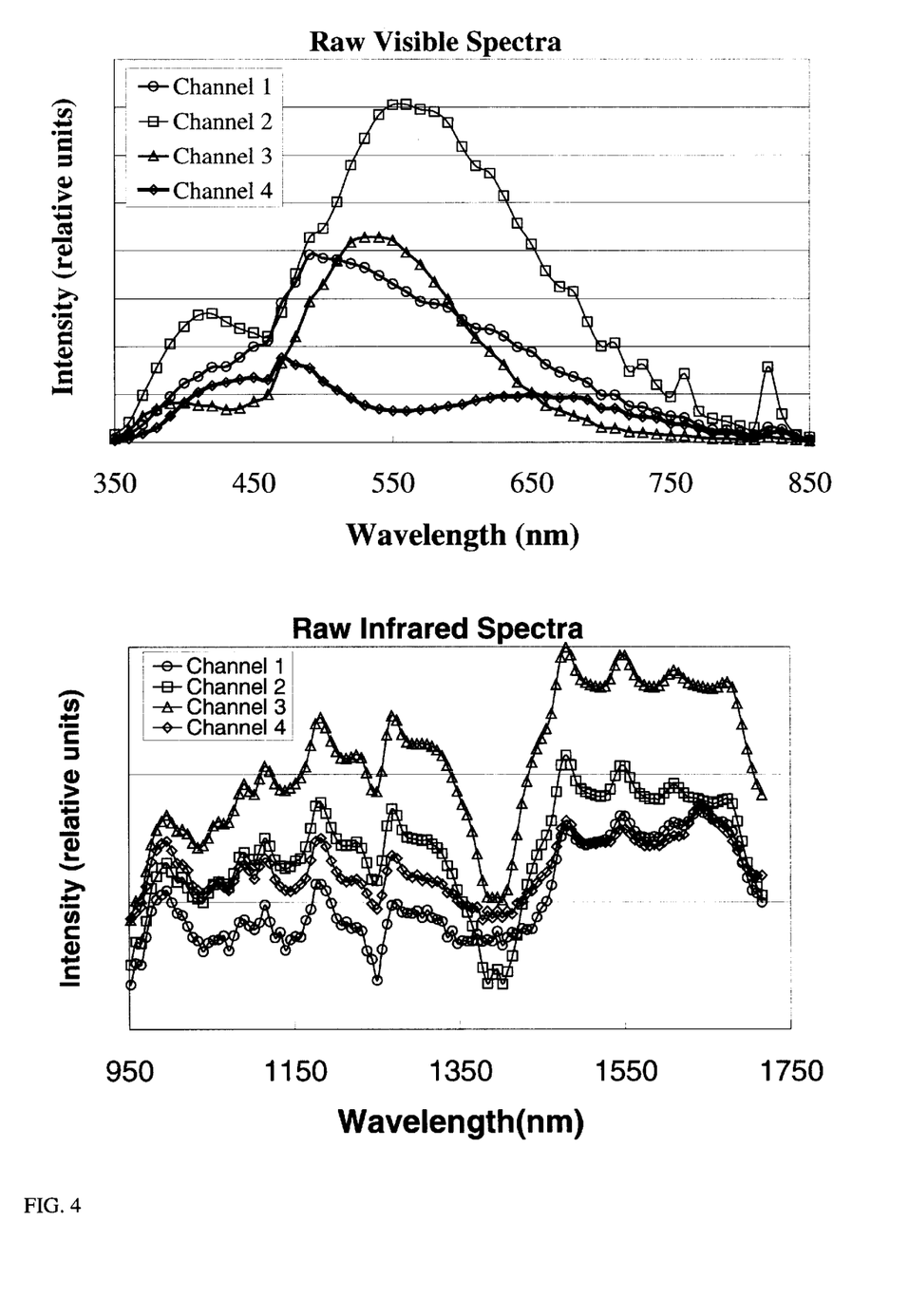
FIG. 4 shows two sets of four graphical representations of raw spectral data obtained from representative samples using the parallel detecting spectroscopic ellipsometer/polarimeter optical system of the present invention.
Figure 5:
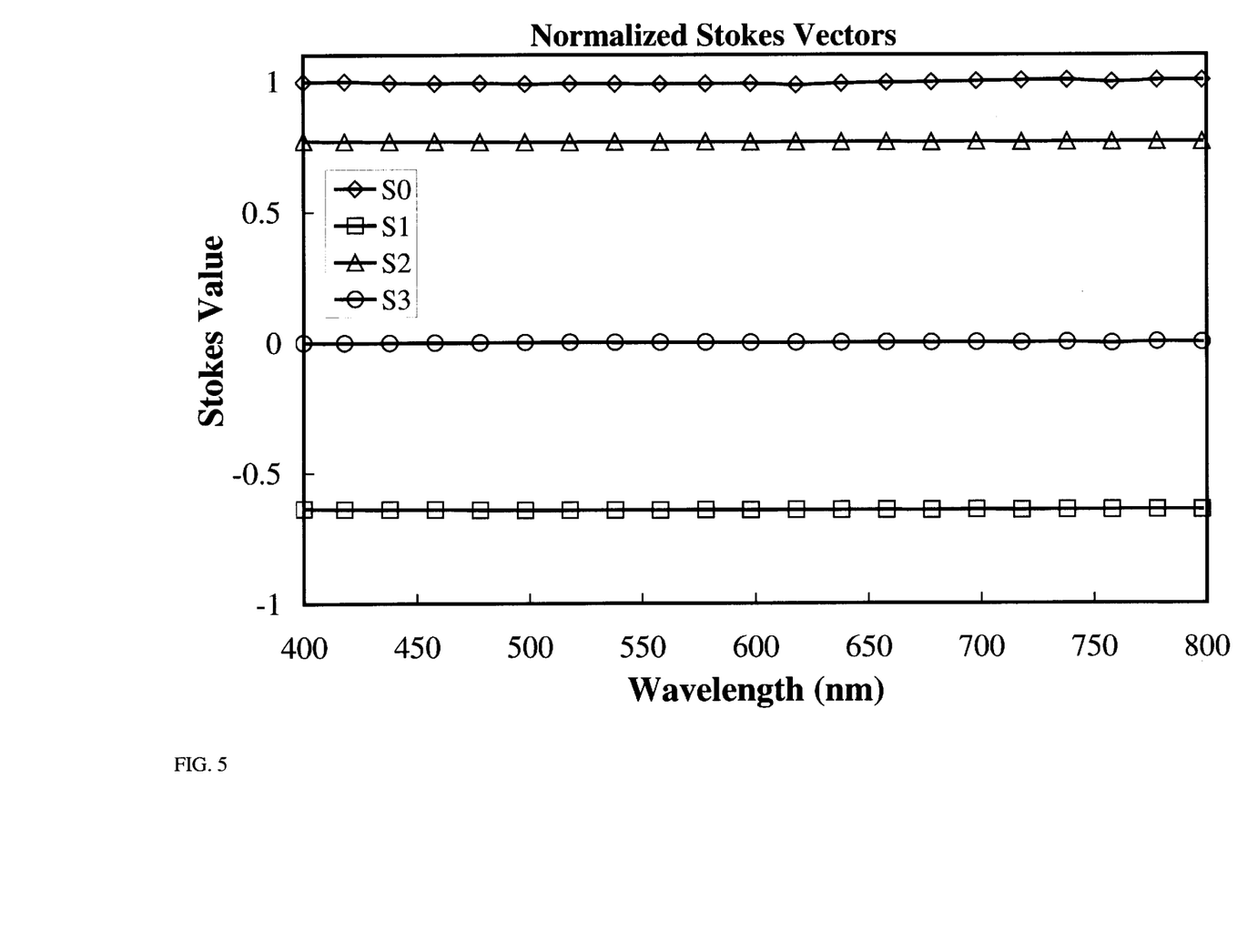
FIG. 5 shows a graphical representation of measured Normalized Stokes Vector values of data collected from 65° linear polarized light and converted via an instrument matrix.
Figure 6:
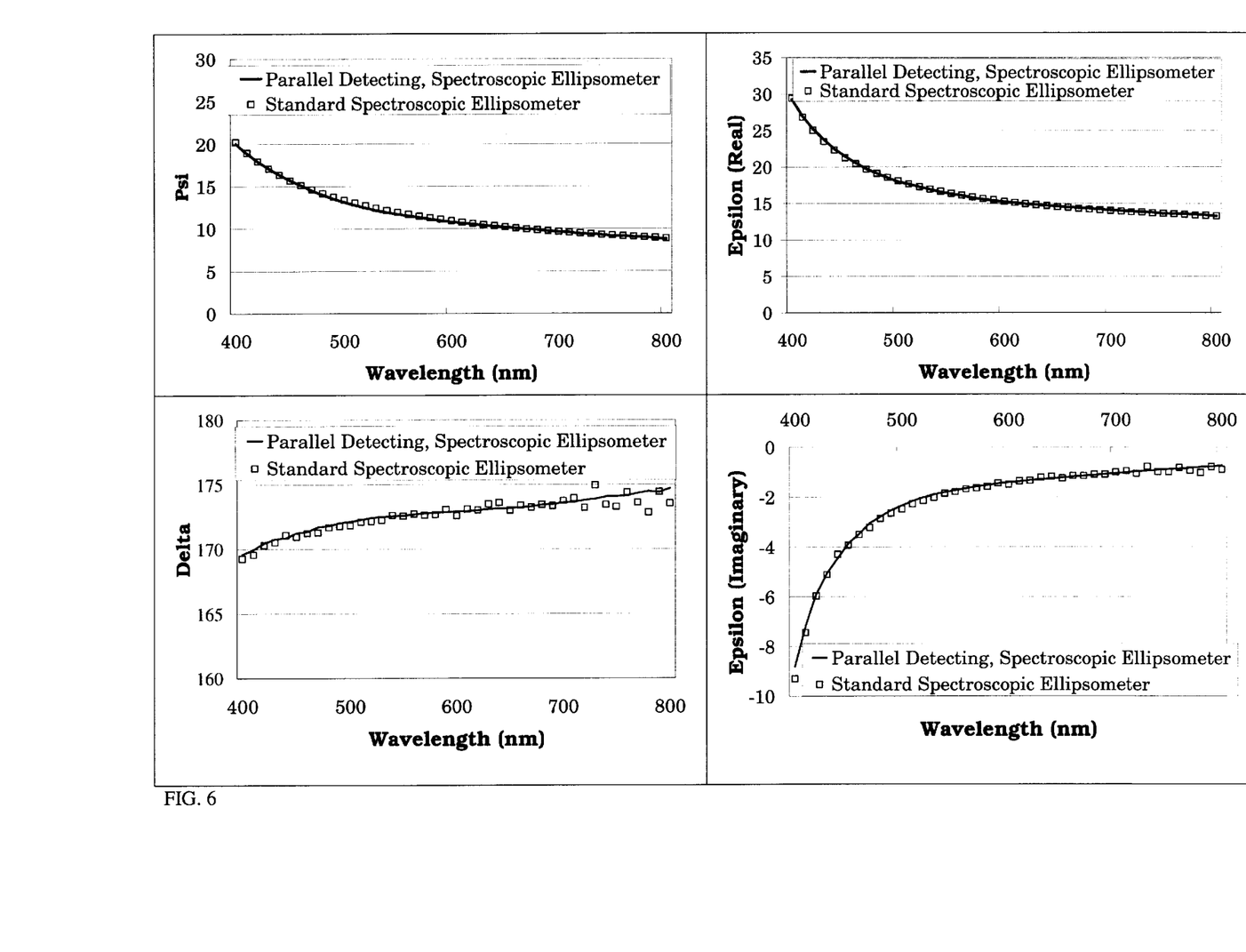
FIG. 6 shows four graphical representations of measured ellipsometry parameters Psi and Delta and the corresponding material properties $\epsilon_1$ and $\epsilon_2$.

As illustrated in the embodiment of FIG. 3, the parallel detecting spectroscopic ellipsometer/polarimeter system of the present invention normally includes multiple spectrometers which are computer operated, and in which the raw data, such as that shown in FIG. 4, is converted to Stokes parameters, as shown in FIG. 5 and/or elipsometric or material property parameters, as shown in FIG. 6, via pre-calibrated instrument matrices. As a substitute for multiple spectrometers a single spectrometer with a switch or allotted area for each spectrum, not shown, may be used.

The data shown in FIG. 4 were obtained from a flexible CuInGaSe$_2$ (CIGS) sample and represent the "raw" spectral distributions of the four polarization states that comprise the complete polarization information. The four intensities, $\vec{I} = (i_0\ i_1\ i_2\ i_3)^T$, measured by the parallel detecting spectroscopic ellipsometer of the present invention are linearly related to the Stokes parameters of the incident light by $$\vec{I} = A\vec{S} \tag{1}$$

where $\vec{S} = (s_0\ s_1\ s_2\ s_3)^T$, and the calibration matrix, A, also known as the instrument matrix, is a 4×4 real matrix characterizing the detection head at a given wavelength. Conversely, the Stokes parameters of the incident light, at a given wavelength, can be determined by $$\vec{S} = A^{-1}\vec{I} \tag{2}$$

The first component of $\vec{S}$ is the incident irradiance while the other three components specify the polarization state. The second component, $s_1$, specifies the tendency of the polarization towards horizontal ($s_1>0$) or vertical ($s_1<0$). It is zero if the polarization does not exhibit any preference to either of these axes. Similarly, $s_2>0$ when the state of polarization is more towards +45°, $s_2<0$ when it is more towards −45°, and $s_2=0$ when it is neither. Also, $s_3>0$ when the incident light is more right circularly polarized, $s_3<0$ when more left circularly polarized and $s_3=0$ when the beam has no preference to either left or right circular polarization.

The first column of A represents the response of the detector head to unpolarized incident light. The second column represents the differential response to orthogonal linear polarizations at 0° and 90° azimuths, while the third column represents the differential response to orthogonal linear polarizations at 45° and 135° azimuths. The fourth column signifies the differential response between the left and right circularly polarizations. The data shown in FIG. 5 were taken with 65° linear polarized light and indicate that the instrument matrix removes the wavelength dependence of the detection optic, thus providing the appropriate Stokes values for all wavelengths in the measurement.

3. Calibration

In principle, the instrument matrix at a given wavelength can be found by making four measurements of known polarization states and using the relationship $$A = MN^{-1} \tag{3}$$

where $M = (\vec{I}_1\ \vec{I}_2\ \vec{I}_3\ \vec{I}_4)$ and $N = (\vec{S}_1\ \vec{S}_2\ \vec{S}_3\ \vec{S}_4)$. The polarization states should be selected in such a way that A is non-singular. In practice this procedure needs to be modified. Since the parallel detecting spectroscopic ellipsometer/polarimeter measures the full Stokes vector it is necessary to either include the absolute intensities in the calibration Stokes vectors or divide the measured intensities by an appropriate normalization factor. The latter is easier to implement and thus most commonly used. For the parallel detecting spectroscopic ellipsometer/polarimeter of the present invention, five light polarization states are used instead of four with the fifth state acting as the intensity standard.

Thus equation (3) becomes $$A = M'N^{-1} \tag{4}$$

where M' is the normalized version of M. For an element $$I'_{ij} = \frac{I_{ij}}{I^0_j},\ 1 \le i,\ j \le 4,$$

$I^0_j$ are the unknown intensity normalization factors. To determine these four unknowns, the fifth measurement is taken for a known polarization state with $\vec{I}_5$ the measured intensity vector and $\vec{S}_5$ the corresponding Stokes vector. From equations (1) and (4)

$$(M'N^{-1})\vec{S}_5 = \vec{I}_5 \tag{5}$$

The unknown intensity normalization factors, $I^0_j$, are obtained by solving the system of equations given by equation (5). This is simultaneously done for each wavelength under consideration.

The four other polarization states used for the calibration need to be selected judiciously, but can be any number of states. If these four states are represented on a Poincaré sphere, then they should form a tetrahedron spanning the largest volume possible. A Poincaré sphere is simply a three dimensional representation of polarization space with pure right and left circular polarization at the poles, pure linear polarization along the equatorial plane, and with the center representing completely unpolarized light. Any set of four polarization states corresponding to the vertices of a tetrahedron of sufficiently large volume can be used. For example, the polarization states including linearly polarized light at 45°, 90°, left circularly polarized light, and right circularly polarized light can be used. Linearly polarized light at 65° can then be used for intensity normalization. Circular polarization states are obtained by using linear polarization states at ±45° with a quarter-wave plate, at 0° azimuth, inserted after a linear polarizer used for calibration, hereinafter referred to as "the calibrator". Contrarily, linear polarization states at 0 and 45° with circular polarization states obtained with linear polarization states at 0° and 90° and a quarter wave plate at 45° azimuth will also work.

Yet another possibility of generating five different polarization states is to use five samples of known, but different optical properties. Each sample will produce a different polarization state and thus they can be used for calibration. Additional samples would need to be used to determine other geometric parameters of the system. Additionally, it is possible to use less polarization states in the calibration procedure by better defining the polarization state of the light from the source, e.g. using an appropriate depolarizer, or, depending on the application, it might be possible to further reduce the number of polarization states.

Although the wavelength dependency of the quarter-wave plate retardance does not have a substantial effect on the calibration it does reduce the volume of the Poincaré sphere enclosed. For a quarter-wave plate $$d(|n_o - n_e|) = (4m+1)\lambda_o/4 \quad (6)$$

where d is the thickness of the material, $n_e$ and $n_o$ are the two principal indices of refraction, $\lambda_o$ is the wavelength in vacuum, and m=0, 1, 2, . . . Using equation (6) the quarter-wave plate retardance (in degrees) at wavelength $\lambda_i$ can be determined:

$$\delta_i = \left(\frac{\lambda_o}{4}\right)\left(\frac{360}{\lambda_i}\right)^\circ \quad (7)$$

The circular polarization states are obtained by using linear polarization states at ±45° with a quarter-wave plate, at 0° azimuth, inserted after the linear polarizer. The angle between the quarter-wave plate fast axis and the transmission axis of the polarizer may deviate from 45° by an angle γ, which can be quantified and incorporated into the calibration. A component or a combination of the components of the normalized Stokes vector can be used in conjunction with a convenient orientation of the quarter-wave plate and the polarizer to determine γ. For example, γ can be derived from the third component of the normalized Stokes vector, $s_3 = p\sin(2Q-2P)$, where p is the degree of polarization given by $\sqrt{(s_1^2 + s_2^2 + s_3^2)/s_0^2}$, P is the azimuth of the polarizer, and Q is the azimuthal angle of the quarter-wave plate fast axis. If the linear polarizer is set at 90° with the quarter-wave plate at 0° azimuth placed after the polarizer then Q=γ. Ideally the normalized Stokes vector should be (1−1 0 0). Any deviation from this will be due to the non-zero value of γ. For given values of p and P, Q and γ can be determined from $s_3$. γ and $\delta_i$ are then incorporated in the instrument matrices through $M_{\lambda_i}$, the Mueller matrix of the quarter-wave plate at wavelength $\lambda_i$ by:

$$M_{80\ i} = R(-\gamma)M_q(\delta_i)R(\lambda) \quad (8)$$

where $$R(\gamma) = \begin{pmatrix} 1 & 0 & 0 & 0 \\ 0 & \cos 2\gamma & \sin 2\gamma & 0 \\ 0 & -\sin 2\gamma & \cos 2\gamma & 0 \\ 0 & 0 & 0 & 1 \end{pmatrix},$$

and $$M_q(\delta_i) = \begin{pmatrix} 1 & 0 & 0 & 0 \\ 0 & 1 & 0 & 0 \\ 0 & 0 & \cos\delta_i & \sin\delta_i \\ 0 & 0 & -\sin\delta_i & \cos\delta_i \end{pmatrix}.$$

In equation (3) $N = (\vec{S}_1\ \vec{S}_2\ \vec{S}_3\ \vec{S}_4)$, where $\vec{S}_1 = (1\ 0\ 1\ 0)^T$, $\vec{S}_2 = (1\ -1\ 0\ 0)^T$, $\vec{S}_3 = (1\ 0\ 0\ 1)^T$, and $\vec{S}_4 = (1\ 0\ 0\ -1)^T$. Note that the right circularly polarized light was obtained by using a linearly polarized light at −45° with the quarter-wave plate inserted after the polarizer. Thus $$\vec{S}_3 = M_q(90°)(1\ 0\ -1\ 0)^T, \text{i.e.}$$

$$\vec{S}_3 = \begin{pmatrix} 1 & 0 & 0 & 0 \\ 0 & 1 & 0 & 0 \\ 0 & 0 & 0 & 1 \\ 0 & 0 & -1 & 0 \end{pmatrix}(1\ 0\ -1\ 0)^T = (1\ 0\ 0\ 1)^T$$

$\vec{S}_4$ is obtained in a similar way. This implies that for each wavelength $\lambda_i$ vectors $(1\ 0\ -1\ 0)^T$ and $(1\ 0\ 1\ 0)^T$ have to be premultiplied by $M_{\lambda_i}$ to obtain $\vec{S}_3$ and $\vec{S}_4$, respectively. Once this is done the instrument matrices are obtained using the procedure in step 1. Saving the intensities measured in step 1 and using them again can save considerable time.

After determining the instrument matrices the remaining three unknown parameters, α, the polarizer azimuth, φ the angle of incidence, and β, the zero azimuth of the calibrator, are determined. One way to determine these values is to collect data from a sample with known optical properties and calculate the appropriate parameters. Given a sample with known optical properties, the Stokes vector, as a function of α, β, and φ, can be evaluated by $$\vec{S}_f = R(\beta)M_s(\phi)R(-\alpha)PR(\alpha)\vec{S}_i \quad (9)$$

where $$R(\alpha) = \begin{pmatrix} 1 & 0 & 0 & 0 \\ 0 & \cos 2\alpha & \sin 2\alpha & 0 \\ 0 & -\sin 2\alpha & \cos 2\alpha & 0 \\ 0 & 0 & 0 & 1 \end{pmatrix},$$

$$P = \frac{1}{2}\begin{pmatrix} 1 & 1 & 0 & 0 \\ 1 & 1 & 0 & 0 \\ 0 & 0 & 0 & 0 \\ 0 & 0 & 0 & 0 \end{pmatrix},$$

and

-continued $$M_s(\phi) = \begin{pmatrix} 1 & \frac{|\rho|^2-1}{|\rho|^2+1} & 0 & 0 \\ \frac{|\rho|^2-1}{|\rho|^2+1} & 1 & 0 & 0 \\ 0 & 0 & \frac{2\text{Re}(\rho)}{|\rho|^2+1} & \frac{2\text{Im}(\rho)}{|\rho|^2+1} \\ 0 & 0 & -\frac{2\text{Im}(\rho)}{|\rho|^2+1} & \frac{2\text{Re}(\rho)}{|\rho|^2+1} \end{pmatrix}.$$

R is the rotation matrix, P is the polarizer matrix with $\alpha=0$, $M_s$ is the Mueller matrix of the sample, $\vec{S}_f$ is the measured Stokes vector, and $\vec{S}_i$ is the Stokes vector of the incident light equal to $(s_{i0}\ 0\ 0\ 0)^T$ assuming unpolarized light. The normalized components of $\vec{S}_f$ are: $s_0=1$ $$s_1 = \frac{(|\rho|^2\cos^2\alpha - \sin^2\alpha)\cos2\beta + \text{Re}(\rho)\sin2\alpha\sin2\beta}{|\rho|^2\cos^2\alpha + \sin^2\alpha} \quad (10)$$

$$s_2 = \frac{-(|\rho|^2\cos^2\alpha - \sin^2\alpha)\sin2\beta + \text{Re}(\rho)\sin2\alpha\cos2\beta}{|\rho|^2\cos^2\alpha + \sin^2\alpha}$$

$$s_3 = \frac{-\text{Im}(\rho)\sin2\alpha}{|\rho|^2\cos^2\alpha + \sin^2\alpha}$$

It is well known that $\rho=\tan(\psi)e^{i\Delta}$, and $\rho$ is a function of $\phi$. For a two phase system (substrate and ambient), such as a silicon wafer, the pseudo[]electric constant is given by $$\langle \varepsilon_m \rangle = \sin^2\phi_m \left[ \left( \frac{1-\rho_m}{1+\rho_m} \right)^2 \tan^2\phi_m + 1 \right] \quad (11)$$

and $$\rho = \frac{\sin\phi\tan\phi - \sqrt{\langle\varepsilon_m\rangle - \sin^2\phi}}{\sin\phi\tan\phi + \sqrt{\langle\varepsilon_m\rangle - \sin^2\phi}}. \quad (12)$$

From the previously measured data, $\langle\varepsilon_m\rangle$ is calculated using equation (11). $\alpha$, $\beta$, and $\phi$ in equations (10) and (12) are then adjusted to minimize deviation between the experimental and known optical parameters. Since the polarization state of the light ($S_0$, $S_1$, $S_2$, $S_3$) is completely determined with the detection component of the parallel detecting spectroscopic ellipsometer/polarimeter of the present invention, once $\alpha$, $\beta$, and $\phi$ are determined for a given configuration, $\rho$ and thus $\psi$ and $\Delta$ or the pseudo-dielectric parameters, can be calculated by:

$$\rho = \frac{ps_0 + s_1\cos2\beta - s_2\sin2\beta}{s_1\sin2\beta + s_2\cos2\beta + is_3}\tan\alpha, \quad (13)$$

where p is the degree of polarization defined earlier. Thus, while the parallel detecting spectroscopic ellipsometer/polarimeter of the present invention is capable of providing ellipsometry measurements of a sample, the detection head is intrinsically calibrated and provides the Stokes parameters as a function of wavelength regardless of the source of the source of polarized light, thus acting independently as a spectroscopic polarimeter.

4. Interpretive Algorithms

Typically, several possible interpretive algorithm procedures can be used to transform in real time the data from the parallel detecting spectroscopic ellipsometer of the present invention to film property values that can be used for feedback/feedforward process control. These include:

First principle advanced algorithm models.
Empirical model, based on measurements, integral part of most transformation strategies
Normal spectral linear regression, usually too long for real time monitoring
Wavelength by wavelength analysis, good for determining optical constants, not real-time
Spectral regression with virtual interface, good when only a single parameter changes
Neural networks, emphasizes principle parameter/component/error analysis
Combination of algorithms, e.g. neural network with one regression.

As an example, the fabrication of flexible CIGS photovoltaic films involves the deposition of a CIGS thin film onto a molybdenum film deposited on a polyimide flexible substrate. To illustrate the capabilities of a parallel detecting spectroscopic ellipsometer/polarimeter of the present invention several CIGS samples with different properties were made and tested. The Cu/(In+Ga) composition ratio of four samples along with the Ga/(In+Ga) ratio of two of these samples were known prior to the ellipsometry tests. Ellipsometry measurements were performed with six CIGS samples. The known composition ratios along with the measured ellipsometry results are shown in Table 1. The ellipsometry results were obtained from a systematic analysis of the raw data that included extraction of the physical contributions. The measured composition ratios, CIGS film thickness, surface roughness and measured band gap results were determined for each of the samples and are tabulated in Table 1.

TABLE 1

Measured Ellipsometer Results from CIGS Samples. The band gap was calculated with the equation Eg = 1.0032 + 0.71369y, y = Ga/(In + Ga); except a356, where Eg = 1.011 + 0.664y + 0.249y(y−1). (Note: + = 'good', o = 'moderate', − = 'poor')

| | Ga/(In + Ga) | | Cu/(In + Ga) | | Quality | | Physical (nm) | | |
|---|---|---|---|---|---|---|---|---|---|
| Sample | Optical | Given | Optical | Given | Optical | Given | Thickness | Roughness | Band Gap |
| a306 | 0.29 | | 0.77 | | o | | 3100 | 85 | 1.21 |
| a336 | 0.24 | 0.15–0.25 | 0.69 | 0.88 | + | + | 1610 | 112 | 1.17 |
| a343 | 0.25 | | 0.77 | | + | | 2000 | 157 | 1.18 |
| a356 | 0.26 | | 0.96 | 1.14 | − | | 1650 | 160 | 1.14 |
| a358 | 0.24 | 0.20–0.40 | 0.91 | 0.91 | + | + | 1690 | 110 | 1.17 |
| a375 | 0.19 | | 0.59 | 0.67 | o | | 3200 | 120 | 1.14 |

Figure 7:
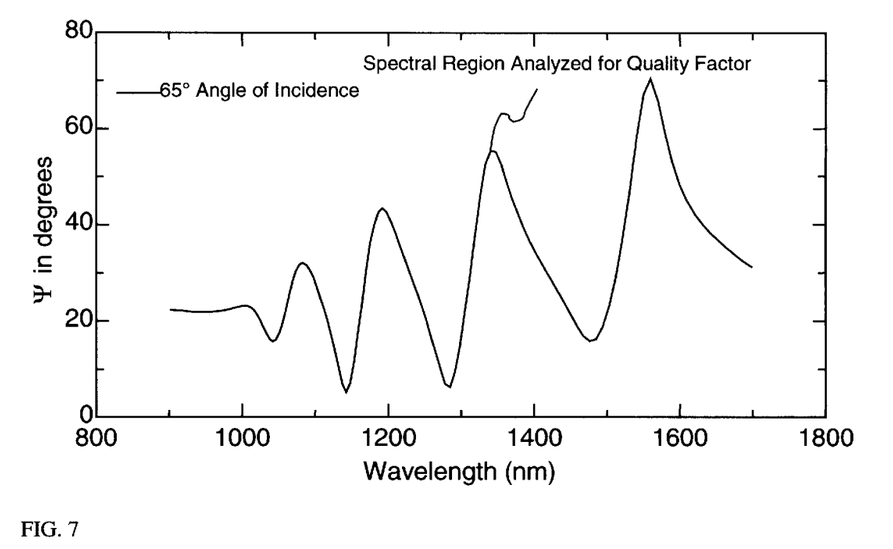
FIG. 7 shows data that illustrates how a spectral fingerprint can be used to design interpretive algorithms.

The optical properties not only contain a great deal of information about the nature of the sample but can also serve as an indicator of quality control. The nature and shape of the oscillations in the parallel detecting spectroscopic ellipsometer/polarimeter data (FIG. 7) is related to the quality factor that has been identified as a useful predictor of the performance of these films in photovoltaic applications. A complete analysis involves processing these data through the instrumentation matrix to extract the complex dielectric function and, from that, the material-dependent properties of the device. A spectrum consisting of the pair of tables $\psi(1)$ and $\Delta(1)$ is sensitive to almost any physical or electronic property that is of interest to a materials processor.

Provided that a spectrum can be rapidly obtained, it is possible to design interpretation algorithms that automatically identify the features of interest. In addition, a spectral fingerprint (FIG. 7) can be used as a "good sample" versus "bad sample" identifier. The special fingerprint approach was demonstrated with CIGS samples.

Figure 8:
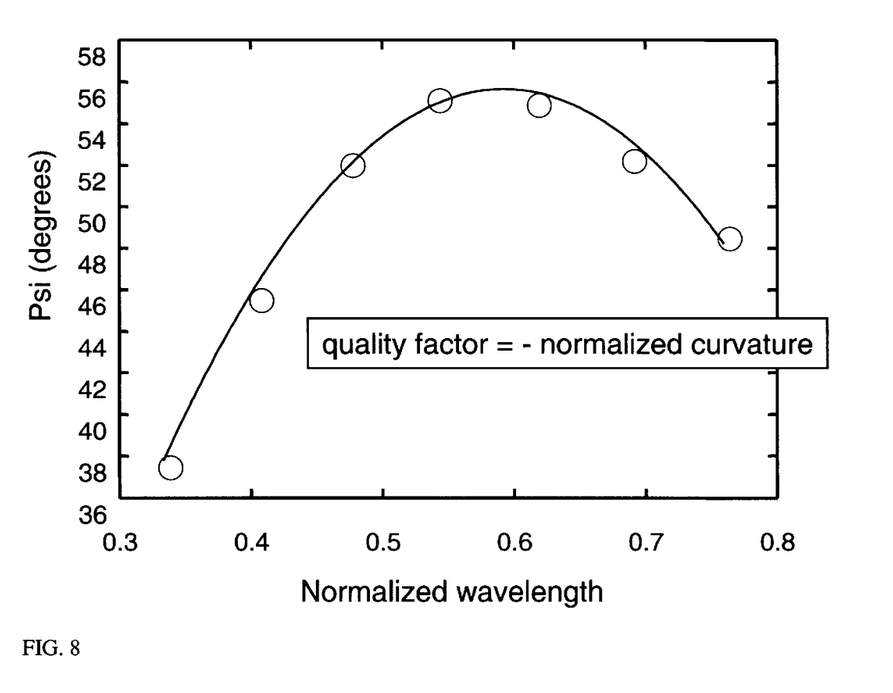
FIG. 8 is a representative plot used to generate a quality factor for samples with slightly different film properties.
Figure 9:
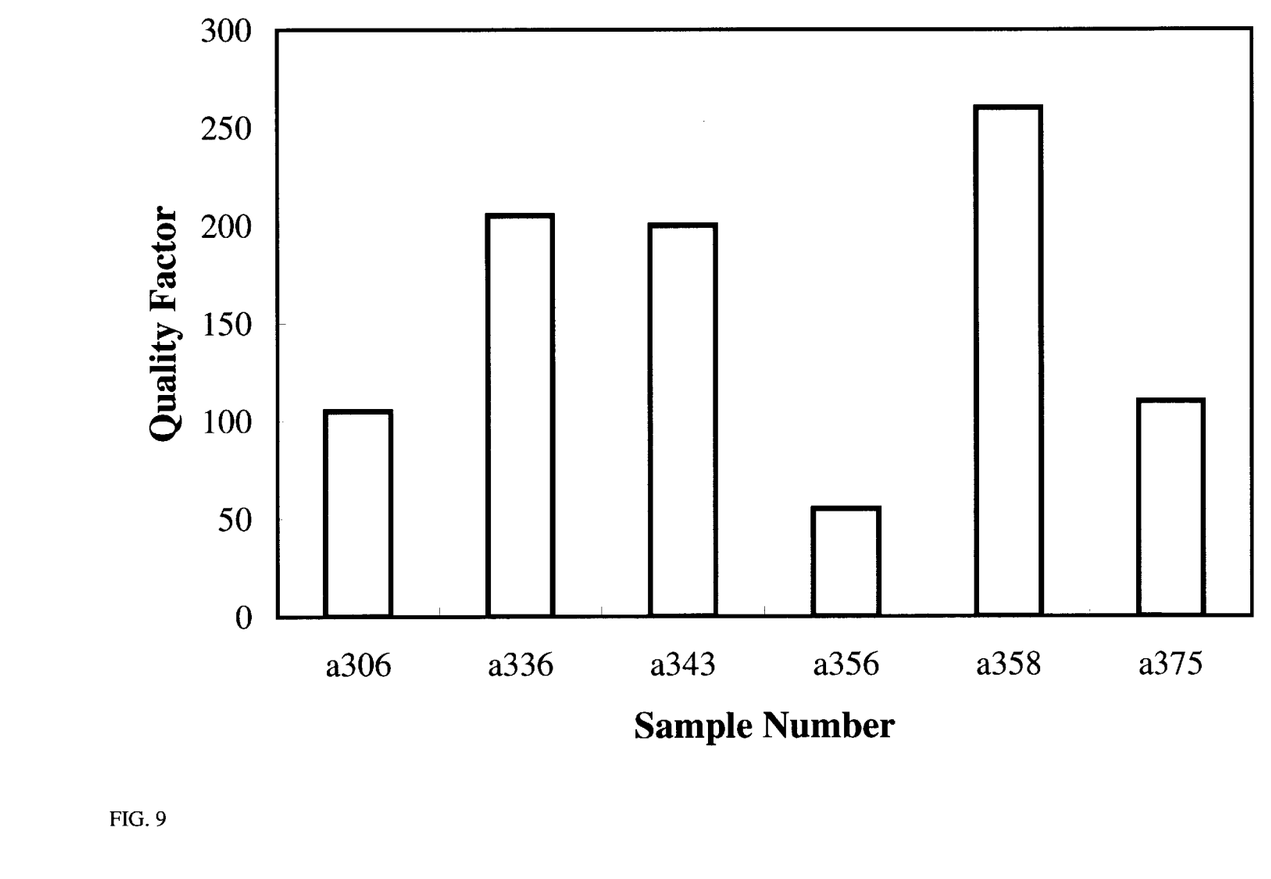
FIG. 9 shows an application of a quality factors to determine sample performance

An ellipsometry spectrum of each CIGS sample was used along with interpretive algorithms to generate a quality factor (FIG. 8). By comparing a specific quality factor from different samples, a criterion can be established to differentiate between "good" and "bad" samples. A comparison between quality factors for CIGS samples is shown in FIG. 9 and summarized in Table 1. The measured ellipsometry quality factor results are in good agreement with the other assessments of the samples shown in Table 1.

This data shows how even a simple analysis of spectroscopic ellipsometry data can lead to valuable insight about a sample that could not be extracted with other sensor methods and can be used for feedback/feedforward process control.

The information from the parallel detecting spectroscopic ellipsometer/polarimeter sensor of the present invention can then be used for real-time feed back/feed forward intelligent process control in the manner set forth in the DISCLOSURE, above. For example, the system has utility in monitoring the rate of growth/thickness/microstructure/surface morphology/voids/ fractures/ composition, and so on, of a thin-film during its formation by any film formation process. Ancillary to the process is both human and software monitoring of the thin-film growth, and, termination of the film formation process when the desired film properties or thickness are detected.

4. Additional Configurations and Applications

While two preferred embodiments of the system have been shown, there are numerous modifications to the present optical configurations that can be made, depending on the physical constraints of the application. For example, if speed is less an issue than cost or wavelength resolution, instead of four spectrometers, one spectrometer may be used in conjunction, for example with an optical switch, fiber optic coupler or segmentation of a CCD array into four separate regions for the four separate spectra. Furthermore, the same principles can be applied to a division of wave-front type instrument where polarizing optics split the incident wave front into separate parts and pass the individual parts through different polarizing filters. The specific intensities collected would then be treated the same as in the "division of amplitude" type instrument described in the preferred embodiment of the present invention.

Different optical collection configurations may be used with or without optic fibers. The spectrometers could be mounted directly with the collection optics and additional polarizers, beam splitters, quarter wave plates, and advanced optical manipulation schemes can be used depending upon the specfic incident polarization and the specfic information desired. Also, variable incident and collection angle configurations will be used. Other ways to remove alignment, i.e. angle sensitivity, may be used including: integrating spheres, large fiber optics, fiber bundles, larger incident light source diameter, holographic filters, different diffuser plates, and the like equivalents. Furthermore, as noted above, different optical configurations may be used for alignment, including the use of a corner cube, imaging cameras, additional laser alignment schemes, and additional direct analysis schemes that monitor the detected intensities or the reflected light itself. The collection head can be used separately, coupled by a telescope to a self-luminous source, or to a source that receives its light by an external mechanism not part of the parallel detecting spectroscopic ellipsometer/polarmeter. This configuration would enable a variety of remote sensing applications such as in target detection or environmental monitoring. Other modifications include the use of additional light sources and different incident polarization schemes including, for example the modulation of the incident polarization to determine the entire Mueller matrix spectrum of the sample.

It is thus seen that the present invention teaches calibration procedures for ellipsometers which are neither complex nor inefficient, and which are capable of simultaneously determining the calibration parameters for the entire spectral range of the instrument in real time for each calibration. More specifically, the present invention teaches a combined parallel detecting spectroscopic ellipsometer/polarimeter sensor system using as many as four state polarization filtering in a manner which substantially decreases spectroscopic polarization data collection time, and which also provides true multispectral analysis of polarization data, in real-time, using advanced transformation algorithms for thousands of wavelengths simultaneously. The present invention further teaches a design which allows it to be integrated within a thin film processing chamber. In addition, spectroscopic ellipsometers of the present invention teaches are capable of polarimetry or simultaneous collection of polarization state information.

While the invention has been so shown, described and illustrated, it should be understood by those skilled in the art, that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. Parallel detecting spectroscopic ellipsometer/polarimeter sensors having no moving parts for real-time monitoring of the properties of the surface of a sample while outside or inside a material deposition chamber during deposition including:

a multi-spectral source of radiation for producing a collimated beam of radiation directed towards the surface of a sample;

polarizing optics through which the collimated beam of multi-spectral radiation is passed before it impacts the surface of a sample at a single incident angle and is reflected from the surface of a sample, at which surface the polarization state of the spectral radiation will be changed due to the intrinsic material properties of the sample;

optic means which splits any spectral radiation reflected from the surface of sample into four separate polarized filtered beams;

optical filter means for each of any said four separate polarized filtered beams for producing four separate beams having individual spectral intensities;

means for collecting data about all of any said four individual spectral intensities, said collecting means being integrated within a material deposition chamber;

means for transmitting any data about all of any said four individual spectral intensities, said transmitting means being operatively associated with said data collecting means;

one or more spectrometer for receiving spectral intensity data from said transmitting means; and means for analyzing any data about four individual spectral intensities using advanced transformation algorithms in real-time, and capable of producing sample specific information by integrating any collected data from all wavelengths.

2. The parallel detecting spectroscopic ellipsometer/polarimeter sensors of claim 1 wherein said source of multi-spectral radiation is a white light source.

3. The parallel detecting spectroscopic ellipsometer/polarimeter sensors of claim 2 wherein said white light source is selected from the group consisting of tungsten halogen lamps, xenon arc lamps, mercury lamps, and other sources of multi-wavelength light.

4. The parallel detecting spectroscopic ellipsometer/polarimeter sensors of claim 1 wherein said optical filter means for one or more of said four separate polarized filtered beams for producing four beams having individual spectral intensities are selected from the group including polarizers, wave retarders, fiber optics, and electrooptics.

5. The parallel detecting spectroscopic ellipsometer/polarimeter sensors of claim 1 wherein said means for analyzing the data of all four individual spectral intensities in real-time includes at least one spectrometer.

6. The parallel detecting spectroscopic ellipsometer/polarimeter sensors of claim 5 wherein said means for analyzing the data of all four individual spectral intensities in real-time includes four spectrometers, one for each of the four individual spectral intensities.

7. The parallel detecting spectroscopic ellipsometer/polarimeter sensors of claim 1 wherein said means for analyzing the data of all four individual spectral intensities in real-time includes one or more computer.

8. The parallel detecting spectroscopic ellipsometer/polarimeter sensors of claim 1 wherein said radiation source and said data collecting means are combined into a single unit, including integrated thin-film optics.

9. The parallel detecting spectroscopic ellipsometer/polarimeter sensors of claim 1 wherein said radiation source and said data collecting means are used for optical analysis selected from the group selected from reflectance spectroscopy and the Mueller matrix spectrum determination.

10. The parallel detecting spectroscopic ellipsometer/polarimeter sensors of claim 1 wherein said data collecting means are used for polarimetry, including the analysis of radiation transmitted through a sample.

11. The parallel detecting spectroscopic ellipsometer/polarimeter sensors of claim 1 wherein said sensor systems have no mechanically moving elements.

12. Methods for parallel detecting spectroscopic ellipsometeric/polarimetry for real-time monitoring of the properties of a sample while within or outside a material deposition chamber including the steps of providing:

a multi-spectral source of radiation for producing a collimated beam of radiation directed towards a sample;

polarizing the collimated beam of multi-spectral radiation before it impacts and is reflected from a sample, at which sample the polarization state of the spectral radiation will be changed due to the intrinsic material properties of the sample;

splitting any spectral radiation reflected from a sample into four separate polarized filtered beams;

filtering any said four separate polarized filtered beams to produce four separate beams having individual spectral intensities;

collecting data about all of any said four individual spectral intensities;

transmitting any data about all of any said four individual spectral intensities;

receiving and analyzing spectral intensity data about any of said four individual spectral intensities using advanced transformation algorithms in real-time, and capable of producing sample specific information by integrating any collected data from all wavelengths.

13. The methods of claim 12 wherein said multi-spectral radiation is white light.

14. Parallel detecting spectroscopic ellipsometer/polarimeter sensors having no moving parts for real-time monitoring of the properties of a sample while outside a material deposition chamber during deposition including:

a multi-spectral source of radiation for producing a collimated beam of radiation directed towards a sample;

polarizing optics through which the collimated beam of multi-spectral radiation is passed before it impacts a sample at a single incident angle and is reflected from a sample, at which sample the polarization state of the spectral radiation will be changed due to the intrinsic material properties of the sample;

optic means which splits any spectral radiation reflected from the sample into four separate polarized filtered beams;

optical filter means for each of any said four separate polarized filtered beams for producing four separate beams having individual spectral intensities;

means for collecting data about all of any said four individual spectral intensities, said collecting means being integrated within a material deposition chamber;

means for transmitting any data about all of any said four individual spectral intensities, said transmitting means being operatively associated with said data collecting means;

one or more spectrometer for receiving spectral intensity data from said transmitting means; and means for analyzing any data about four individual spectral intensities using advanced transformation algorithms in real-time, and capable of producing sample specific information by integrating any collected data from all wavelengths.

\* \* \* \* \*